United States Patent [19]

Seidelmann et al.

[11] Patent Number: 4,719,210
[45] Date of Patent: Jan. 12, 1988

[54] 3-VINYL AND 3-THYINYL-BETA-CARBOLINES, AND THEIR USE AS BENZODIAZEPINE RECEPTOR ANTAGONISTS OR AGONISTS

[75] Inventors: Dieter Seidelmann; Andreas Huth; Ralph Schmiechen; Rudolf Wiechert; Herbert Schneider; David N. Stephens, all of Berlin, Fed. Rep. of Germany

[73] Assignee: Schering Aktiengesellschaft, Berlin and Bergkamen, Fed. Rep. of Germany

[21] Appl. No.: 915,360

[22] Filed: Oct. 6, 1986

[30] Foreign Application Priority Data

Oct. 4, 1985 [DE] Fed. Rep. of Germany ....... 3535927

[51] Int. Cl.⁴ ................. A61K 31/435; A61K 31/38; A61K 31/495; C07D 471/04
[52] U.S. Cl. ..................... 514/222; 514/237; 514/239; 514/227; 514/253; 514/292; 514/63; 546/14; 546/85; 546/86; 546/87; 544/60; 544/126; 544/361
[58] Field of Search ............... 546/85, 86, 87, 14; 544/60, 126, 361; 514/237, 239, 227, 222, 253, 292, 63

[56] References Cited

PUBLICATIONS

Chem. Abstracts, vol. 98, 16663c (1983).
Chem. Abstracts, vol. 101, 151824b (1984).

Primary Examiner—Alan L. Rotman
Assistant Examiner—J. Richter
Attorney, Agent, or Firm—Millen & White

[57] ABSTRACT

Compounds of formula I

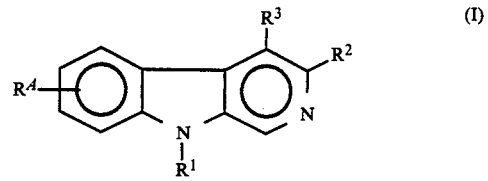

wherein
$R^1$ is hydrogen or a protecting group,
$R^2$ is —CH=$CR_2^4$ or —C≡$CR^4$,
$R^4$ is hydrogen or halogen,
$R^3$ is hydrogen, lower alkyl or lower alkoxyalkyl,
$R^4$ is, inter alia, hydrogen, $OR^7$, lower alkyl, which optionally is substituted with aryl, lower alkoxy or NR5R6,
$R^5$ and $R^6$ can be the same or different and in each case is hydrogen, lower alkyl or together with the nitrogen atom a 5–6 member ring, which can contain another heteroatom,
$R^7$ is lower alkyl, optionally substituted aryl or aralkyl, and
each compound can contain one or more $R^4$ radicals which are not hydrogen, have valuable pharmacological properties.

14 Claims, No Drawings

3-VINYL AND 3-THYINYL-BETA-CARBOLINES, AND THEIR USE AS BENZODIAZEPINE RECEPTOR ANTAGONISTS OR AGONISTS

This invention relates to new 3-vinyl- and 3-ethinyl-beta-carboline derivatives, their production and their use as drugs.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been achieved by providing new compounds according to the invention of the formula I

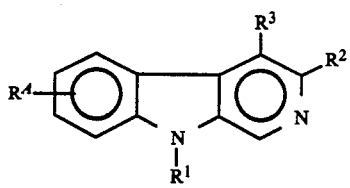

wherein
- $R^1$ is hydrogen or a protecting group (e.g., for amino),
- $R^2$ is $-CH=CR_2^4$ or $-C\equiv CR^4$,
- $R^4$ is hydrogen or halogen (F, Cl, Br, I),
- $R^3$ is hydrogen, lower alkyl or lower alkoxyalkyl,
- $R^4$ is hydrogen, $OR^7$, lower alkyl, $NR_5R_6$, or lower alkyl which optionally is substituted with aryl, substituted aryl, lower alkoxy or, $NR_5R_6$,
- $R^5$ and $R^6$ can be the same or different and in each case are hydrogen, lower alkyl or together with the nitrogen atom form a 5-6 member ring, which can contain another heteroatom,
- $R^7$ is lower alkyl, optionally substituted aryl or aralkyl, and
- each compound can contain one or more $R^4$ radicals which are not hydrogen.

The compounds according to the invention have valuable pharmacological properties. They affect especially the central nervous system and thus are suitable as psychotropic drugs.

The new 3-vinyl- or 3-ethinyl-beta-carboline derivatives of formula I can be substituted one or several (up to 4) times in the A ring in positions 5-8. Substitution in the 5, 6 or 7 position is preferred. 1-2 substituents are preferred.

All lower alkyl portions of all groups include both straight-chain and branched radicals of $C_1-C_6$ carbon atoms. For example, preferred $C_{1-4}$ alkyl radicals can be mentioned such as methyl, ethyl, n-propyl, isopropyl, n-butyl, isobutyl and tert-butyl etc. Pentyl and hexyl groups are also suitable. The total number of C atoms in alkoxyalkyl groups is usually 2-6.

As $R^2$ halogens bromine and chlorine are preferred.

If $R^5$ and $R^6$ together with the nitrogen atom form a heterocycle, then the latter can optionally also contain another nitrogen, oxygen or sulfur atom. For example, the following heterocycles are suitable as radicals: pyrrolidine, piperazine, morpholine, thiomorpholine and piperidine.

Typically, the heterocyclic rings are saturated, aliphatic moieties. They typically are bonded via a C-atom but can also be bonded by a hetero N-atom.

All aryl groups (in $R^7$ or as alkyl substituents) can be substituted one or several times (e.g., 1-2) by halogen, for example, fluorine, chlorine, bromine or iodine, by $C_{1-2}$ alkyl or by $C_{1-2}$ alkoxy groups. Suitable aryl groups are of 6-10 C-atoms, e.g., phenyl, naphthyl.

Aralkyl radicals $R^7$ preferably have 1-2 carbon atoms in the alkyl portion: for example, benzyl and phenethyl radicals, 1-phenethyl and 2-phenethyl.

It is known that certain sites in the central nervous system of vertebrates exhibit a great specific affinity for the binding of 1,4- and 1,5-benzodiazepines (Squires, R. F. and Braestrup, C., Nature (London) 266 (1977) 734). The binding sites are called benzodiazepine receptors.

It was found that the substituted beta-carbolines according to the invention, although they greatly differ in their chemical structure from benzodiazepines, surprisingly exhibit a strong affinity and specificity for binding on the benzodiazepine receptors. This can be shown by their displacing radioactively marked flunitrazepam for these benzodiazepine receptors.

The displacement activity of the compounds according to the invention can be indicated as an $IC_{50}$ or $ED_{50}$ value. The $IC_{50}$ value indicates the concentration which causes a 50% displacement of the specific binding of $^3$H-flunitrazepam (1.0 nM, 0° C.) in samples with a total volume of 0.55 ml of a suspension of brain membranes, e.g., of rats. The displacement activity is determined in the in vitro test as follows: 0.5 ml of a suspension of untreated rat forebrain in 25 mM $KH_2PO_2$, pH=7.1 (5-10 mg tissue/sample) is incubated for 40-60 minutes at 0° C. together with $^3$H-diazepam (specific activity 14.4 Ci/mmol, 1.9 mM) or $^3$H-flunitrazepam (specific activity 87 Ci/mmol, 1.0 nM). After incubation, the suspension is filtered through a glass filter, the residue is washed twice with cold buffer solution and the radioactivity is measured on the scintillation counter. The test was then repeated but before addition of the radioactive benzodiazepine a specific amount or an excess amount of the compound whose displacement activity is to be determined, is added. The $IC_{50}$ value is calculated on the basis of the values obtained. The $ED_{50}$ value represents the dose of a test substance which causes a reduction of the specific binding of the flunitrazepam on the benzodiazepine receptor in a live brain to 50% control value.

The in vivo test is performed as follows:

The test substance is injected into groups of mice in different doses and normally subcutaneously. After 15 minutes, the $^3$H-flunitrazepam is administered intravenously to the mice. After another 20 minutes, the mice are sacrificed, their forebrain is removed and the radioactivity specifically linked to the forebrains is measured by scintillation counting. The $ED_{50}$ value is determined from the dose/action curves.

On the basis of their biological effectiveness the compounds according to the invention are useful as psychotropic drugs for human medicine. For this purpose, they can be formulated in psychopharmaceutical preparations, and administered for example, by oral or parenteral application.

Physiologically compatible organic or inorganic vehicles which are inert in regard to the compounds according to the invention are suitable as inactive formulation ingredients.

Suitable vehicles include, for example, water, salt solutions, alcohols, polyethylene glycols, polyhydroxyethoxylated castor oil, gelatins, lactose, amylose, magnesium stearate, talc, silicic acid, fatty acid mono and diglycerides, pentaerythritol fatty acid ester, hydroxymethylcellulose and polyvinylpyrrolidone. The pharmaceutical preparations can be sterilized and/or mixed with inactive ingredients such as lubricants, preservatives, stabilizers, wetting agents, emulsifiers, buffering agents and dyes.

For parenteral application especially suitable are injection solutions or suspensions, especially aqueous solutions of the active compounds in polyhydroxyethoxylated castor oil. For oral application especially suitable are tablets, sugar-coated tablets or capsules with talc and/or a hydrocarbon vehicle or binding agent, such as, for example lactose, corn or potato starch. The administration can take place also in liquid form, for example, as a juice to which, optionally, a sweetening agent is added.

The compounds according to the invention can be used in a unit dose of 0.05 to 100 mg of active substance in a physiologically compatible vehicle. The compounds according to the invention are administered in a dose of 0.1 to 300 mg/day, preferably 1–30 mg/day.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate conventional pharmacological protocol. The compounds according to the invention are particularly suitable as anxiolytics and antiepileptics at the above mentioned dosages.

All compounds of this invention have affinity for benzodiazepine receptors. Consequently, they have a spectrum of the activities of the benzodiazepines, e.g., muscle relaxant, sedative, anxiolytic or anticonvulsant and are useful for the conventional corresponding indications, e.g., muscle relaxants, antiepileptic, sedatives, hypnotics, tranquilizers, etc. These activities can be from agonistic to antagonistic to inverse agonistic, the corresponding indications being conventional in each case, e.g., antagonistically they can be used to reverse benzodiazepine effects, e.g., in cases of overdose, inverse agonistically they can be used to achieve the inverse effects of the benzodiazepines, e.g., they can be used as vigilance enhancers, etc. The type and level of activity for a given dosage of each compound can be conventionally determined by routine experimentation using well known parmacological protocols for each of the activities; the corresponding indications treatable at that dosage will be well known to skilled workers based on the pharmacological results. The compounds can be administered analogously to the known agent diazepam to treat symptoms such as anxiety with and without depression, epilepsy, sleep disorders, muscle tension, etc.

The production of the compounds according to the invention takes place according to methods known in the art.

For example, the production of the compounds of formula I can take place by a reacting compound of formula II

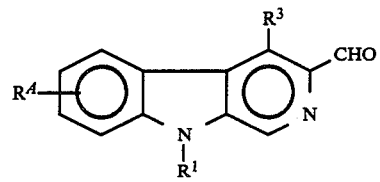

wherein
$R^3$ and $R^4$ have the above-mentioned meanings and
$R^1$ represents a protecting group, with a Wittig reagent to form a compound of formula Ia

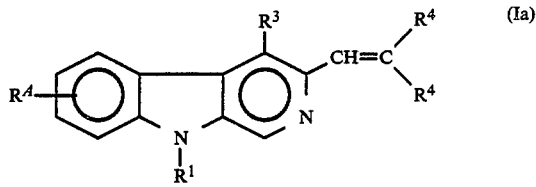

wherein
$R^3$, $R^4$ and $R^A$ have the above-mentioned meanings and
$R^1$ represents a protecting group and, optionally cleaving off the protecting group or, when $R^4$ is halogen, converting the product with bases to form a resulting 3-haloethinyl-beta-carboline derivative which can be dehalogenated and, if desired, hydrogenated.

Before performing the Wittig reaction, it is advantageous to exchange the proton donors present in the molecule for protecting groups according to the usual processes. All protecting groups that are ordinarily used for this purpose, e.g., amino protecting groups are suitable as protecting groups such as, for example, alkyl, acyl, aralkyl, arylsulfonyl or silyl radicals, the arylsulfonyl or trialkylsilyl radicals especially the tosyl radical or the tert-butyl dimethyl silyl radical, being preferred.

For introduction of the vinyl group in the 3 position, the usual Witting reagents are used, for example, triphenylphosphine/tetrahalomethane or alkyl—triphenyl phosphononium halides, whereby halogen preferably is chlorine or bromine. If compounds of formula Ia with $R^4$ being halogen are to be produced, the aldehyde of general formula II is reacted with triphenylphosphine and tetrahalomethane.

The reaction is performed in inert polar solvents at temperatures from −50° C. to the boiling temperature of the reaction mixture, preferably at temperatures from −20° C. to +50° C. Suitable solvents are, for example, chlorinated hydrocarbons such as dichloromethane, dichloroethane; ethers such as diethyl ether, tetrahydrofuran, dioxane; dimethylformamide; dimethylsulfoxide; and the like. The reaction time is 15–20 hours and can be easily accelerated to about 6–8 hours by using ultrasound or by addition of zinc.

If the compounds of general formula Ia with $R^4$ being hydrogen are to be produced, the aldehyde of formula II is reacted with methyltriphenylphosphonium halides, preferably the bromides or chlorides, in the presence of bases. For the production of the -ylene all strong, preferably alkali metal organic bases can be used, as for, example, alkali metal alcoholates such as potassium tert-butylate, lithium organyls such as tert-butyllithium or lithium diisopropylamide, sodium amide or sodium hydride/dimethylsulfoxide but also potassium carbonate or sodium hydroxide. The above-named inert polar solvents, and in particular cases hydrocarbons, for example, hexane or pentane, can be used as solvents. The reaction takes place at temperatures of from −50° C. up to the boiling temperature of the reaction mixture and generally ends after 1–4 hours. The operation advantageously takes place under an inert gas atmosphere, for example, under nitrogen or argon.

The Wittig reaction can be performed in homogeneous or heterogeneous phase. In a two-phase reaction it is also advantageous to add a phase transfer catalyst, for example, a crown ether such as 18-crown-6, dicyclohexyl-18-crown-6, dibenzo-18-crown-6 or Aliquat 336.

If present, protecting group $R^1$ can be cleaved off at room temperature according to the usual methods, for example, by treatment with bases such as sodium or potassium alcoholate or acids such as dilute inorganic acids or trifluoroacetic acid in inert solvents such as alcohols, hydrocarbons, etc.

Hydrogen halide can be cleaved off from the geminal dihalogen compound of formula Ia by reaction with bases as Hydrogen halide can be cleaved off from the geminal dihalogen compound of formula Ia by reaction with bases as elevated temperature (preferably 20° C. to 100° C.). The reaction generally ends after 2–6 hours. For the dehydrohalogenation inorganic or organic bases can be used, for example, potassium hydroxide, sodium hydroxide (in solid form), alkali metal alcoholates such as sodium or potassium ethylate methylate or tert-butylate, alkylated amines such as Huenig base, cyclic amines such as 1,5-diazabicyclo[5.4.0]-undec-5-ene, 1,4-diazabicyclo-[2.2.2]octane, i.a. The dehydrohalogenation can be performed in all inert aprotic and protic solvents, for example, ethers such as diethyl ether, tetrahydrofuran; hydrocarbons such as hexane, pentane, alcohols such as methanol, ethanol, etc. If a protecting group is present in the 9 position, it is cleaved off under the reaction conditions described above. Two-phase reactions with the use of a phase transfer catalyst as described above are also applicable.

The 3-halogen-ethinyl-beta-carboline derivatives of formula I can be converted into the 3-ethinyl-beta-carboline derivatives by reaction with lithium organyls and then decomposed with water. All known lithium organyls can be used for the reaction, lithium phenyl and lithium alkyls such as, for example, tert-butyllithium being preferred. The halogen-lithium exchange is performed at low temperatures (preferably 0° C. to −90° C.) and is ended after ½ hour to 2 hours. Then, stirring is continued for 1–2 hours at room temperature. Advantageously the operation is performed under inert gas atmosphere, for example, under nitrogen or argon. For the dehalogenation aprotic solvents such as ether or hydrocarbons are suitable, for example, tetrahydrofuran, dioxane, diethyl ether, toluene, hexane, etc.

The 3-ethinyl-beta-carboline derivatives can be partially hydrogenated to form 3-vinyl derivatives according to known processes, for example in the presence of Lindlar catalyst or by hydroaluminizing and subsequent protolytic cleaving. The hydrogenation on Lindlar catalysts is performed optionally with the addition of a catalyst poison, for example, quinoline or pyridine at room temperature in an inert solvent, for example, hydrocarbons or alcohols, etc.

The hydroaluminizing can be performed with aluminum organic compounds, for example, diisobutylaluminum hydride at temperatures from −80° C. to room temperature and then heating to up to 80° C. Advantageously, the operation is under protective gas atmosphere in inert solvents as, for example, ethers or hydrocarbons. Cleaving is performed with acids, preferably inorganic acids, for example hydrochloric acid, at room temperature. The initial compounds are known or can be produced according to known processes.

The starting material aldehydes of formula II are known or readily preparable from known starting materials using known reactions, e.g., those described below. See also U.S. Pat. No. 4435403, which discloses compounds of formula II and methods of preparing them.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

Production of initial material
5-benzyloxy-4-methoxymethyl-9-tosyl-beta-carboline-3-carbaldehyde 3.9 g of 5-benzyloxy-4-methoxymethyl-beta-carboline-3-carboxylic acid ethyl ester is dissolved in 70 ml of dichloromethane with 1.84 ml of triethylamine and 0.54 g of dimethylaminopyridine. The solution is cooled to 0° C. and then mixed by portions with 2.54 g of tosyl chloride. After stirring for 2 hours at room temperature and standing overnight, it is shaken out three times with sodium hydrogen carbonate solution, the organic phase is concentrated and recrystallized from acetic acid. 4 g of 5-benzyloxy-4-methoxymethyl-9-tosyl-beta-carboline-3-carboxylic acid ethyl ester with a melting point of 149°–150° C. is obtained. This 4 g is dissolved in 40 ml of tetrahydrofuran under argon and mixed at room temperature with 17 ml of a 1.7 molar solution of calcium diisopropoxy aluminum hydride in tetrahydrofuran (Capal); after refluxing for one hour, 17 ml of Capal is added once more and refluxing is continued for 2 hours. After cooling, it is mixed with 2N sodium hydroxide solution and shaken out with acetic acid. The organic phase is concentrated and 3.1 g of 5-benzyloxy-4-methoxymethyl-9-tosyl-3-hydroxymethyl-beta-carboline is obtained, which is suspended in 57 ml of toluene and mixed with 1 ml of azodicarboxylic acid ester. After refluxing for 12 hours, it is concentrated and chromatographed over silica gel with cyclohexane:acetic acid=1:1 as eluant, 1.8 g of 5-benzyloxy-4-methoxymethyl-9-tosyl-beta-carboline-3-carbaldehyde with a melting point of 125°–127° C. is obtained.

In the same way there are produced:
5-isopropoxy-4-methyl-9-tosyl-beta-carboline-3-carbaldehyde (172°–175° C. mp)
5-phenoxy-4-methoxymethyl-9-tosyl-beta-carboline-3-carbaldehyde (150°–153° C. mp)
5-benzyloxy-9-tosyl-beta-carboline-3-carbaldehyde (185°–187° C. mp)
6-benzyloxy-4-methoxymethyl-9-tosyl-beta-carboline-3-carbaldehyde (188°–190° C. mp)
6-phenoxy-4-methoxymethyl-9-tosyl-beta-carboline-3-carbaldehyde 6-isopropoxy-4-methoxymethyl-9-tosyl-beta-carboline-3-carbaldehyde
6-phenoxy-4-methyl-9-tosyl-beta-carboline-3-carbaldehyde
6-(4-chlorophenoxy)-4-methoxymethyl-9-tosyl-beta-carboline-3-carbaldehyde (215°-217° C. mp)
6-phenoxy-9-tosyl-beta-carboline-3-carbaldehyde
6,7-dimethoxy-9-tosyl-4-ethyl-beta-carboline-3-carbaldehyde
5-(1-ethoxyethyl)-4-methyl-9-tosyl-beta-carboline-3-carbaldehyde
5-(methoxymethyl)-4-methyl-9-tosyl-beta-carboline-3-carbaldehyde
5-(morpholinomethyl)-4-methyl-9-tosyl-beta-carboline-3-carbaldehyde
6-piperidino-4-methyl-9-tosyl-beta-carboline-3-carbaldehyde
5-ethyl-4-methyl-9-tosyl-beta-carboline-3-carbaldehyde.

The following examples are to explain the process according to the invention.
5(-4-fluoro benzyloxy)-4-methoxymethyl-9-tosyl-beta-carboline-3-carbaldehyde (170°-172° C. mp)
5-(-4-chlorophenoxy)-4-methoxymethyl-9-tosyl-beta-carboline-3-carbaldehyde.

EXAMPLE 1

5-Benzyloxy-3-(1,1-dibromovinyl)-4-methoxymethyl-9-tosyl-beta-carboline 2.5 g of 5-benzyloxy-4-methoxymethyl-9-tosyl-beta-carboline-3-carboxaldehyde and 2.6 g of triphenylphosphine are dissolved in 27 ml of dichloromethane and cooled to +5° C. 1.82 g of tetrabromomethane, dissolved in 7 ml of dichloromethane, is added drop by drop to this solution with stirring, so that the reaction temperature of +5° C. is not exceeded. After the addition is completed, the reaction mixture is stirred for 16 hours at room temperature, the solvent is evaporated and the residue is chromatographed over silica gel with dichloromethane/ethanol=1000+25 as eluant. 2 g of 5-benzyloxy-3-(1,1-dibromovinyl)-4-methoxymethyl-9-tosyl-beta-carboline with a melting point of 149°-152° C. is obtained.

EXAMPLE 2

Analogously to example 1 there were produced:
5-isopropoxy-3-(1,1-dibromovinyl)-4-methoxymethyl-9-tosyl-beta-carboline
5-phenoxy-3-(1,1-dibromovinyl)-4-methoxymethyl-9-tosyl-beta-carboline (mp 179°-182° C.)
5-(4-chlorophenoxy)-3-(1,1-dibromovinyl)-4-methoxymethyl-9-tosyl-beta-carboline (mp 165°-167° C.)
5-benzyloxy-3-(1,1-dibromovinyl)-4-methyl-9-tosyl-beta-carboline
5-isopropoxy-3-(1,1-dibromovinyl)-4-methyl-9-tosyl-beta-carboline (mp 168°-172° C.)
5-phenoxy-3-(1,1-dibromovinyl)-4-methyl-9-tosyl-beta-carboline
5-benzyloxy-3-(1,1-dibromovinyl)-9-tosyl-beta-carboline (mp 160°-162° C.)
6-benzyloxy-3-(1,1-dibromovinyl)-4-methoxymethyl-9-tosyl-beta-carboline
6-phenoxy-3-(1,1-dibromovinyl)-4-methoxymethyl-9-tosyl-beta-carboline
6-isopropoxy-3-(1,1-dibromovinyl)-4-methoxymethyl-9-tosyl-beta-carboline
6-phenoxy-3-(1,1-dibromovinyl)-4-methyl-9-tosyl-beta-carboline
6-(4-chlorophenoxy)3-(1,1-dibromovinyl)-4-methyl-9-tosyl-beta-carboline
5-(4-fluorobenzyloxy)-3-(1,1-dibromovinyl)-4-methoxymethyl-9-tosyl-beta-carboline (144°-145° C. mp)
6-phenoxy-3-(1,1-dibromovinyl)-9-tosyl-beta-carboline
6,7-dimethoxy-3-(1,1-dibromovinyl)-4-ethyl-9-tosyl-beta-carboline
5-(1-ethoxyethyl)-4-methyl-3-(1,1-dibromovinyl)-9-tosyl-beta-carboline
5-methoxymethyl-4-methyl-3-(1,1-dibromovinyl)-9-tosyl-beta-carboline
5-morpholinomethyl-4-methyl-3-(1,1-dibromovinyl)-9-tosyl-beta-carboline
6-piperidino-4-methyl-3-(1,1-dibromovinyl)-9-tosyl-beta-carboline
5-ethyl-4-methyl-3-(1,1-dibromovinyl)-9-tosyl-beta-carboline.

EXAMPLE 3

1-bromo-2-(5-benzyloxy-4-methoxymethyl-beta-carbolin-3-yl)acetylene

A solution of 0.141 g of sodium in 12 ml of methanol is added drop by drop with stirring to a solution of 2 g of 5-benzyloxy-3-(1,1-dibromovinyl)-4-methoxymethyl-9-tosyl-beta-carboline in 25 ml of methanol. The reaction is stirred at room temperature for 3 hours and then evaporated to dryness. The residue is chromatographed over silica gel with dichloromethane/ethanol=10/1 as eluant. 0.7 g of 1-bromo-2-(5-benzyloxy-4-methoxymethyl-beta-carbolin-3-yl)acetylene with a melting point of 160° C. is obtained (decomposition).

EXAMPLE 4

Analogously to example 3 there were produced:
1-bromo-2-(5-isopropoxy-4-methoxymethyl-beta-carbolin-3-yl)acetylene
1-bromo-2-(5-phenoxy-4-methoxymethyl-beta-carbolin-3-yl)acetylene. 210°-212° C. (decomposition)
1-bromo-2-[5-(4-chlorophenoxy)-4-methoxymethyl-beta-carbolin-3-yl]acetylene. 207°-209° C. (decomposition)
1-bromo-2-(5-benzyloxy-4-methyl-beta-carbolin-3-yl)acetylene
1-bromo-2-(5-isopropoxy-4-methyl-beta-carbolin-3-yl)acetylene. 170° C. (decomposition)
1-bromo-2-[5-(4-fluorobenzyloxy)]-4-methoxymethyl-beta-carbolin-3-yl)acetylene. 151°-153° C. (decomposition)
1-bromo-2-(5-phenoxy-4-methyl-beta-carbolin-3-yl)acetylene. 188° C. (decomposition)
1-bromo-2-(5-benzyloxy-beta-carbolin-3-yl)acetylene
1-bromo-2-(6-benzyloxy-4-methoxymethyl-beta-carbolin-3-yl)acetylene. 177°-180° C. (decomposition)
1-bromo-2-(6-phenoxy-4-methoxymethyl-beta-carbolin-3-yl)acetylene
1-bromo-2-(6-isopropoxy-4-methoxymethyl-beta-carbolin-3-yl)acetylene
1-bromo-2-(6-phenoxy-4-methyl-beta-carbolin-3-yl)acetylene
1-bromo-2-[5-(4-chlorophenoxy)-4-methyl-beta-carbolin-3-yl]acetylene
1-bromo-2-(6-phenoxy-beta-carbolin-3-yl)acetylene 1-bromo-2-(6,7-dimethoxy-4-ethyl-beta-carbolin-3-yl)acetylene 1-bromo-2-[5-(1-ethoxyethyl)-4-methyl-beta-carbolin-3-yl]acetylene 1-bromo-2-(5-methoxymethyl-4-methyl-beta-carbolin-3-yl)acetylene 1-bromo-2-(5-morpholinomethyl-4-methyl-beta-carbolin-3-yl)acetylene 1-bromo-2-(6-piperidino-4-methyl-beta-carbolin-3-yl)acetylene 1-bromo-2-(5-ethyl-4-methyl-beta-carbolin-3-yl)acetylene.

EXAMPLE 5

5-Benzyloxy-3-ethinyl-4-methoxymethyl-beta-carboline

A solution of 0.164 g of 1-bromo-2-(5-benzyloxy-4-methoxymethyl-beta-carbolin-3-yl)acetylene in 5 ml of abs. tetrahydrofuran is cooled under $N_2$ atmosphere to −78° C. and mixed with 0.46 ml of a 1.4 molar solution of tertbutyllithium in pentane. After 1 hour stirring at −78° C. the reaction mixture is heated to room temperature and stirred for 1.5 hours more. Then it is carefully decomposed with water and extracted with dichloromethane. The organic phases are combined, dried and the solvent evaporated. The residue is chromatographed over silica gel with acetone/hexane=1+1 as eluant. 0.056 g of 5-benzyloxy-3-ethinyl-4-methoxymethyl-beta-carboline with a melting point of 207°-209° is obtained.

EXAMPLE 6

Analogously to example 5 there were obtained:

5-isopropoxy-3-ethinyl-4-methoxymethyl-beta-carboline 5-phenoxy-3-ethinyl-4-methoxymethyl-beta-carboline. 115° C. (decomposition)

5-(4-chlorophenoxy)-3-ethinyl-4-methoxymethyl-beta-carboline. 260°-263° C. (decomposition)

5-benzyloxy-3-ethinyl-4-methyl-beta-carboline 5-isopropoxy-3-ethinyl-4-methyl-beta-carboline. mp 205°-207° C.

5-phenoxy-3-ethinyl-4-methyl-beta-carboline 5-benzyloxy-3-ethinyl-beta-carboline. mp 206°-210° C.

6-benzyloxy-3-ethinyl-4-methoxymethyl-beta-carboline. mp 205°-209° C.

6-phenoxy-3-ethinyl-4-methoxymethyl-beta-carboline 6-isopropoxy-3-ethinyl-4-methoxymethyl-beta-carboline 6-(4-chlorophenoxy)-3-ethinyl-4-methyl-beta-carboline 6-phenoxy-3-ethinyl-beta-carboline 6,7-dimethoxy-3-ethinyl-4-ethyl-beta-carboline 5-(1-ethoxyethyl)-4-methyl-3-ethinyl-beta-carboline 5-methoxymethyl-4-methyl-3-ethinyl-beta-carboline 5-morpholinomethyl-4-methyl-3-ethinyl-beta-carboline 6-piperidino-4-methyl-3-ethinyl-beta-carboline 5-ethyl-4-methyl-3-ethinyl-beta-carboline 5-(4-fluorobenzyloxy)-3-ethinyl-4-methoxymethyl-beta-carboline. 181°-184° C. (decomposition).

EXAMPLE 7

5-Benzyloxy-4-methoxymethyl-9-tosyl-3-vinyl-beta-carboline 1.0 g of methyltriphenylphosphoniumbromide+sodium amide (condition-ylide) in 8 ml of absolute tetrahydrofuran is stirred at room temperature under argon for 15 minutes. To it is added 500 mg of 5-benzyloxy-4-methoxymethyl-9-tosyl-beta-carboline-3-carbaldehyde and the reaction mixture is refluxed for 4 hours. After evaporation of the solvent, the residue is chromatographed over silica gel with cyclohexane/acetic acid=8+2 as eluant. 0.153 mg of 5-benzyloxy-4-methoxymethyl-9-tosyl-3-vinyl-beta-carboline with a melting point of 141°-143° C. is obtained.

EXAMPLE 8

5-benzyloxy-4-methoxymethyl-3-vinyl-beta-carboline

A solution of 0.23 g of sodium in 10 ml of methanol is added drop by drop with stirring to a suspension of 0.5 g of 5-benzyloxy-4-methoxymethyl-9-tosyl-3-vinyl-beta-carboline in 20 ml of methanol. After 72 hours of stirring at room temperature, it is evaporated to dryness and the residue is chromatographed over silica gel with dichloromethane/ethanol=10/1 as eluant. 0.135 g of 5-benzyloxy-4-methoxymethyl-3-vinyl-beta-carboline with a melting point of 183°-185° C. is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

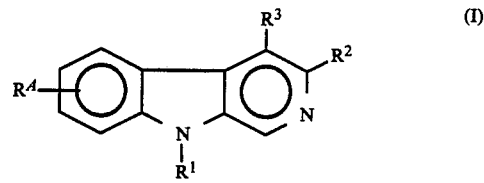

wherein $R^1$ is hydrogen or an alkyl, acyl, aralkyl, arylsulfonyl, or trialkylsilyl amino protective group, $R_2$ is $-CH=C(R^4)_2$ or $-\equiv CR^4$ $R^4$ is hydrogen or halogen, $R^3$ is hydrogen, lower alkyl or lower alkoxyalkyl, $R^4$ is $OR^7$, lower alkyl, or lower alkyl which is substituted by $C_{6-10}$ aryl, substituted $C_{6-10}$-aryl as defined below, lower alkoxy or, $NR_5R_6$, $R_5$ and $R_6$ are the same or different and are hydrogen, lower alkyl or together with the connecting nitrogen atom form pyrrolidine, piperazine, morpholine, thiomorpholine or piperidine, $R^7$ is lower alkyl, $C_{6-10}$-aryl, $C_{6-10}$-ar-$C_{1-4}$-alkyl, or $C_{6-10}$-aryl or $C_{6-10}$-ar-$C_{1-4}$-alkyl each substituted by halogen, $C_{1-2}$-alkyl or $C_{1-2}$-alkoxy, n is 0-4 and $C_{6-10}$-aryl is phenyl or naphthyl.

2. A compound of claim 1 wherein $R^2$ is —CH=O($R^4$)$_2$.

3. A compound of claim 1 wherein $R^2$ is —C≡$CR^4$.

4. A compound of claim 1 wherein $R^4$ is halogen.

5. A compound of claim 1 wherein $R^4$ is Cl or Br.

6. A compound of claim 1 wherein $R^1$ is H.

7. A compound of claim 1 wherein $R^4$ is alkoxy, aryloxy, (substituted aryl)oxy or alkoxyalkyl.

8. 1-Bromo-2-(5-isopropoxy-4-methoxymethyl-beta-carbolin-3-yl)acetylene,
   1-bromo-2-(5-phenoxy-4-methoxymethyl-beta-carbolin-3-yl)acetylene,
   1-bromo-2-[5-(4-chlorophenoxy)-4-methoxymethyl-beta-carbolin-3-yl]acetylene,
   1-bromo-2-(5-isopropoxy-4-methyl-beta-carbolin-3-yl)acetylene,
   1-bromo-2-(6-benzyloxy-4-methoxymethyl-beta-carbolin-3-yl)acetylene,
   1-bromo-2-(6-phenoxy-4-methoxymethyl-beta-carbolin-3-yl)acetylene,
   1-bromo-2-(6-isopropoxy-4-methoxymethyl-beta-carbolin-3-yl)acetylene,
   1-bromo-2-[5-(1-ethoxyethyl)-4-methyl-beta-carbolin-3-yl]acetylene,
   1-bromo-2-(5-methoxymethyl-4-methyl-beta-carbolin-3-yl)acetylene,
   1-bromo-2-(5-morpholinomethyl-4-methyl-beta-carbolin-3-yl)acetylene,
   1-bromo-2-(6-piperidino-4-methyl-beta-carbolin-3-yl)acetylene,
   5-isopropoxy-3-ethinyl-4-methoxymethyl-beta-carboline,
   5-phenoxy-3-ethinyl-4-methoxymethyl-beta-carboline,
   5-(4-chlorophenoxy)-3-ethinyl-4-methoxymethyl-beta-carboline,
   5-isopropoxy-3-ethinyl-4-methyl-beta-carboline,
   6-benzyloxy-3-ethinyl-4-methoxymethyl-beta-carboline,
   6-phenoxy-3-ethinyl-4-methoxymethyl-beta-carboline,
   6-isopropoxy-3-ethinyl-4-methoxymethyl-beta-carboline,
   6-(4-chlorophenoxy)-3-ethinyl-4-methyl-beta-carboline,
   5-methoxymethyl-4-methyl-3-ethinyl-beta-carboline,
   5-morpholinomethyl-4-methyl-3-ethinyl-beta-carboline,
   1-bromo-2-(5-benzyloxy-4-methoxymethyl-beta-carbolin-3-yl)acetylene,
   5-benzyloxy-3-ethinyl-4-methoxymethyl-beta-carboline, or 3-vinyl-5-benzyloxy-4-methoxymethyl-beta-carboline, each a compound of claim 1.

9. A pharmaceutical composition suitable for binding benzodiazepine receptors comprising an amount of a compound of claim 1 effective to bind said receptors, and a pharmaceutically acceptable carrier.

10. A pharmaceutical composition of claim 9 wherein the amount of said compound is 0.05 to 100 mg.

11. A method of binding a benzodiazepine receptor in a patient in need of such treatment comprising administering to the patient an amount of a compound of claim 1 effective for such treatment.

12. A method of achieving an anticonvulsive or antiepileptic effect in a patient in need of such treatment comprising administering to the patient an amount of a compound of claim 1 effective to achieve said effect.

13. A method of claim 12 wherein the effect is anticonvulsive.

14. A method of claim 12 wherein the effect is antiepileptic.

* * * * *